US00PP16488P3

(12) United States Plant Patent
Rockie

(10) Patent No.: US PP16,488 P3
(45) Date of Patent: May 2, 2006

(54) ZOYSIAGRASS PLANT NAMED 'Z-89'

(50) Latin Name: ***Zoysia* sp.**
Varietal Denomination: Z-89

(76) Inventor: John W. B. Rockie, 45-342 Lilipuna Rd., Suite #304, Kaneohe, HI (US) 96744

( * ) Notice: Subject to any disclaimer, the term of this patent is extended or adjusted under 35 U.S.C. 154(b) by 266 days.

(21) Appl. No.: 10/624,966

(22) Filed: Jul. 21, 2003

(65) Prior Publication Data

US 2005/0022281 P1 Jan. 27, 2005

(51) Int. Cl.
*A01H 5/00* (2006.01)

(52) U.S. Cl. ..... Plt./390

(58) Field of Classification Search ..... Plt./390
See application file for complete search history.

*Primary Examiner*—Anne Marie Grunberg
*Assistant Examiner*—Annette H Para
(74) *Attorney, Agent, or Firm*—Christie, Parker & Hale, LLP

(57) ABSTRACT

Described is a new Zoysiagrass variety characterized by a finer leaf texture, an improved color and an improved growth habit compared to other Zoysiagrass varieties.

5 Drawing Sheets

Latin name of genus and species: The present invention relates to a new *Zoysia* sp. plant.

BACKGROUND OF THE INVENTION

The present invention relates to a new and distinct variety of *Zoysia* sp., which is a member of the Graminae family.

The new variety, Z-89, also referred to herein as Z99-89, is the result of five generations of crossing, beginning with a cross of *Z. japonica*×*Z. matrella*, and the reciprocal cross; *Z. tenuifolia* was introduced in the third generation of crosses. The pedigree is shown in FIG. 1. The first cross was field-pollinated. All succeeding generations of crosses were hand-pollinated under greenhouse conditions, and seed was germinated under greenhouse conditions. Seedlings were individually cultured in a greenhouse before being transplanted to the field for evaluation and selection.

Periodic drought conditions in Hawaii have increased the need for improved warm season turfgrass varieties. Zoysiagrasses are well adapted for use under such conditions because of their low water use rates and high heat tolerance.

SUMMARY OF THE INVENTION

The new variety of zoysiagrass, Z-89, exhibits a finer leaf texture, an improved color and an improved growth habit compared to other currently available commercial zoysiagrass varieties. The new variety is vegetatively propagated from sod, plugs, tillers or stolon and rhizome pieces. Asexual propagation in Oahu, Hi. has established that the combination of characteristics of the new variety are transmitted through succeeding generations. However, seed is genetically unstable.

COMPARISON TO EL TORO AND EMERALD

The leaf size is intermediate between its ancestors El Toro and Emerald, giving its appearance a finer texture than El Toro. It possesses the dark green color of El Toro, and lacks the hummocky growth habit and stiff leaf of emerald. The growth rate is also intermediate between El Toro and Emerald.

BRIEF DESCRIPTION OF ILLUSTRATION(S)

DESCRIPTION OF THE NEW VARIETY

Figure 1:
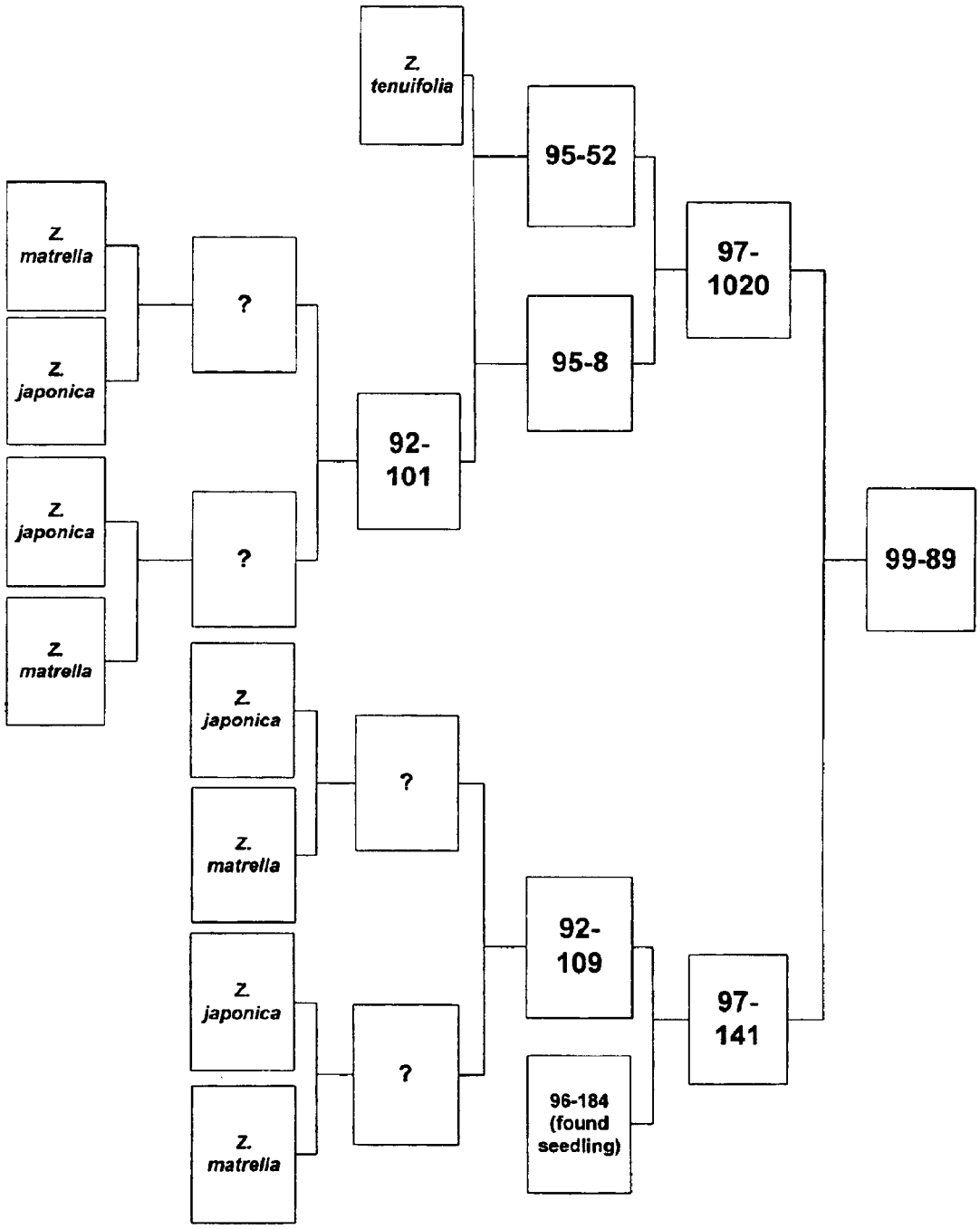
FIG. 1 is a diagram showing the pedigree of Z-89.
Figure 2:
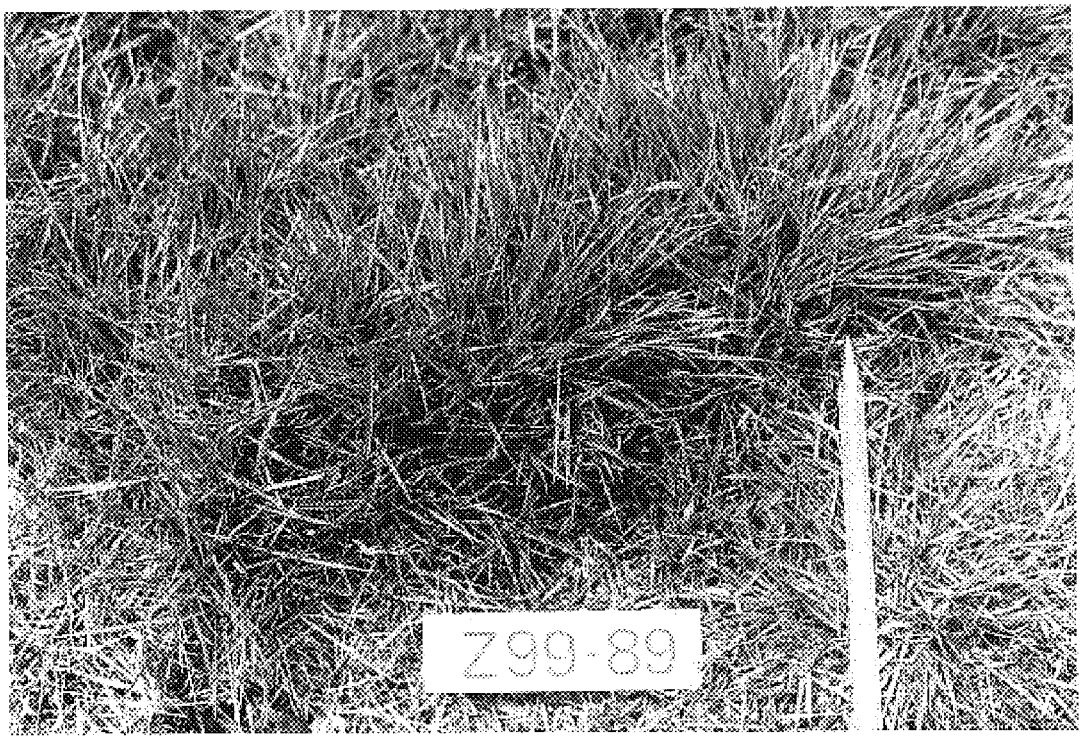
FIG. 2 shows the turf appearance of the new variety.
Figure 3:
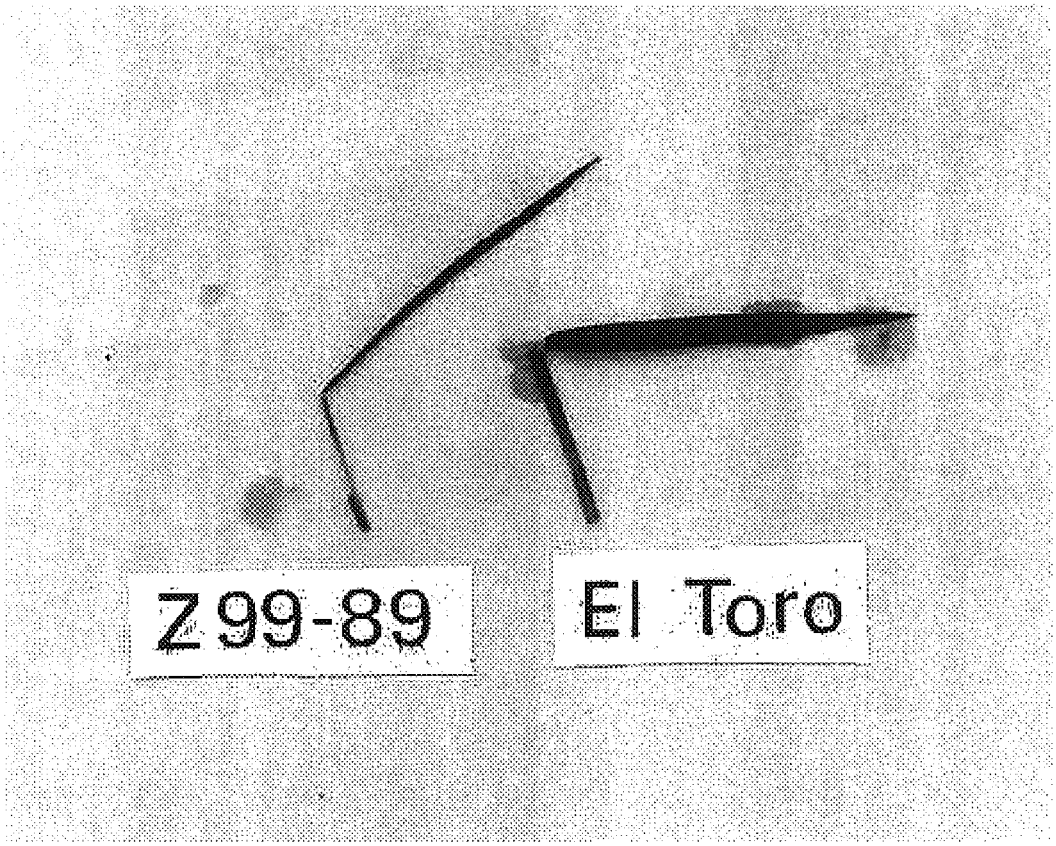
FIG. 3 shows the appearance of a single leaf of the new variety as compared to that of 'El Toro.'
Figure 4:
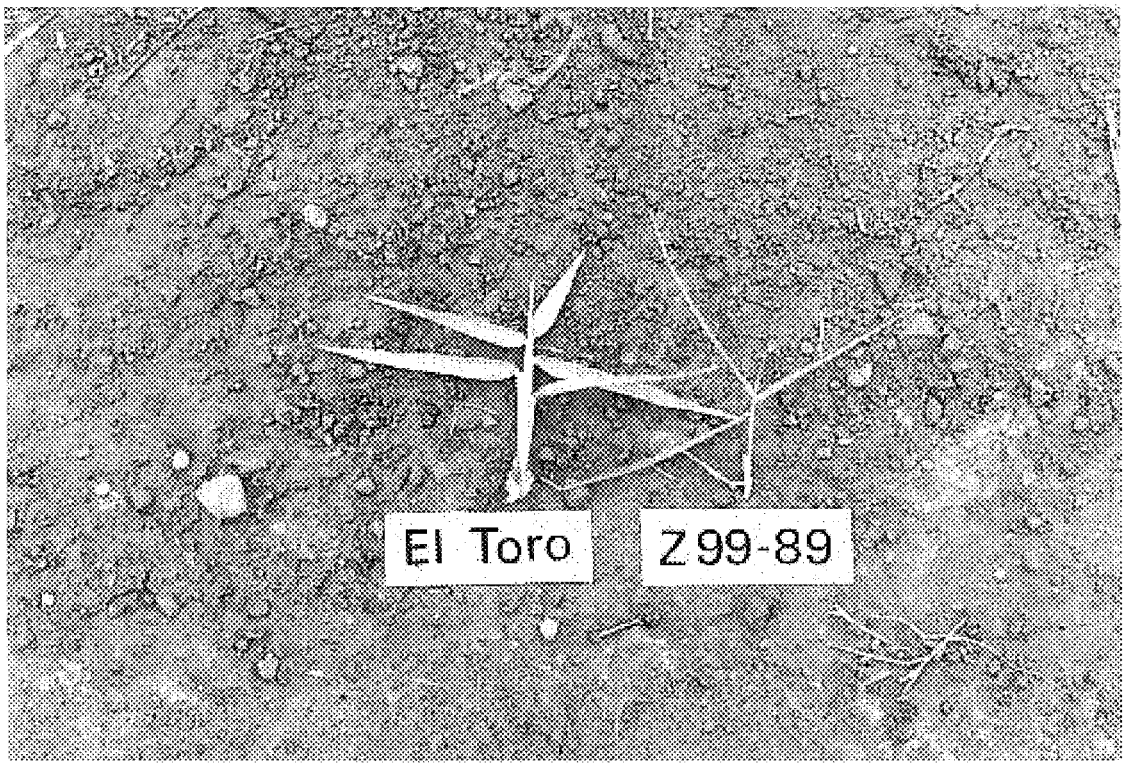
FIG. 4 depicts the leaf orientation of the new variety and of the 'El Toro' variety.
Figure 5:
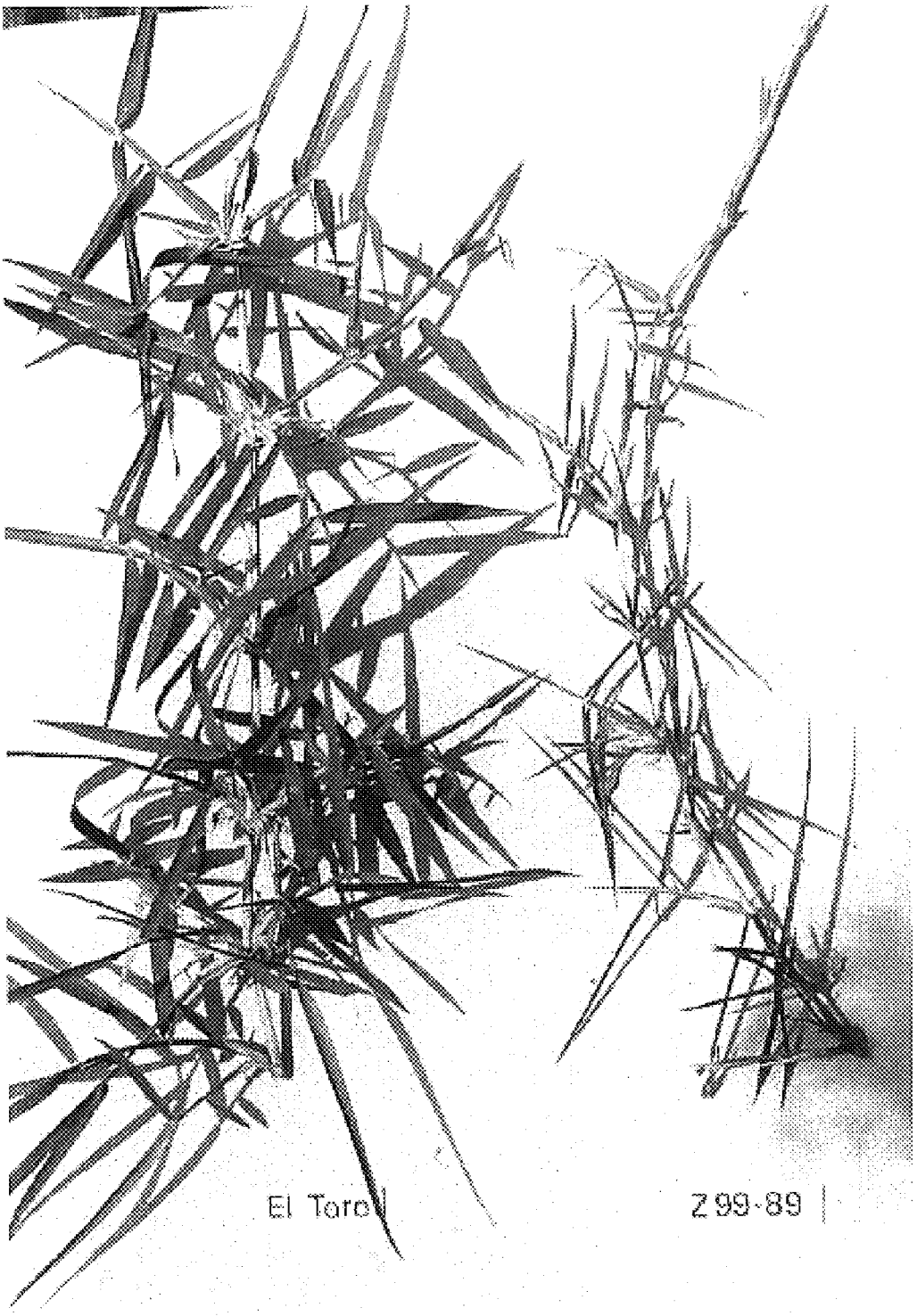
FIG. 5 shows stolons of the new variety compared with 'El Toro.'

The new variety 'Z-89' is characterized by a finer leaf texture, an improved color and an improved growth habit compared to other currently available commercial Zoysiagrass varieties. The following description is of 8 months-old plants grown in Oahu, Hi. with color descriptions in accordance with the Colour Chart of The Royal Horticultural Society, London ($4^{th}$ ed. 1995). All dimensions are in millimeters, weights in grams (unless otherwise stated).

Leaf color: Near 137A (upper surface); near 139A (underside).
Stolon color: Near N79B.
Leaf length: From 3.2 cm to 9.9 cm; average length 5.7 cm.
Leaf width: From 1.5 mm to 3.0 mm; average width 2.2 mm.
Internode length: From 0.4 cm to 2.9 cm; average length 1.7 cm.
Internode thickness: From 1.2 mm to 2.1 mm; average 1.6 mm.
Raceme length: From 2.7 cm to 9.9 cm, average length 5.0 cm.
Culm height: From 7.5 cm to 13.1 cm; average 9.0 cm.
Pedicel: From 1.0 mm to 2.1 mm; average 1.5 mm.
Ligule: Hairs at ligule area from 2.5 mm to 3.0 mm; hairs on side of ligule 0.5 mm to 4.0 mm.
Spikelet with anthers and stigma exerted: Color from near N77C to near N186C.
Mature spikelets: Color from near N79A to near 158A.

Palea and lemma: Color is near N144A. Immature seed color is near N79B. Ripe see color is near 19C. Seeds: About 2.5 to 3 mm in length and 0.5 to 0.75 mm in width.

Winter color retention and spring green-up are impossible to evaluate in Hawaii's climate.

I claim:

1. A new Zoysiagrass plant of the variety substantially as shown and described.

* * * * *